(12) United States Patent  
Clement et al.

(10) Patent No.: US 9,314,275 B2  
(45) Date of Patent: Apr. 19, 2016

(54) VERTEBRAL OSTEOSYNTHESIS EQUIPMENT

(75) Inventors: Jean-Luc Clement, La Colle sur Loup (FR); Afshin Aminian, Santa Ana, CA (US)

(73) Assignee: MEDICREA INTERNATIONAL, Neyron (FR)

( * ) Notice: Subject to any disclaimer, the term of this patent is extended or adjusted under 35 U.S.C. 154(b) by 18 days.

(21) Appl. No.: 14/123,626

(22) PCT Filed: Jun. 13, 2012

(86) PCT No.: PCT/IB2012/052985  
§ 371 (c)(1),  
(2), (4) Date: Dec. 3, 2013

(87) PCT Pub. No.: WO2012/176096  
PCT Pub. Date: Dec. 27, 2012

(65) Prior Publication Data  
US 2014/0094850 A1    Apr. 3, 2014

(30) Foreign Application Priority Data  
Jun. 22, 2011 (FR) ...................................... 11 55504

(51) Int. Cl.  
*A61B 17/70* (2006.01)  
*A61B 17/84* (2006.01)

(52) U.S. Cl.  
CPC ......... *A61B 17/7053* (2013.01); *A61B 17/7001* (2013.01); *A61B 17/7076* (2013.01); *A61B 17/7082* (2013.01); *A61B 17/842* (2013.01)

(58) Field of Classification Search  
CPC ........... A61B 17/7053; A61B 17/8869; A61B 17/8861; A61B 17/7074; A61B 17/82; A61B 17/88; A61B 17/8841; A61B 17/842

USPC ...................................... 606/263, 53, 74, 279  
See application file for complete search history.

(56) References Cited

U.S. PATENT DOCUMENTS

| 5,403,314 A | 4/1995 | Currier |
| 5,417,690 A * | 5/1995 | Sennett et al. .................. 606/74 |

(Continued)

FOREIGN PATENT DOCUMENTS

| EP | 2279707 | 2/2011 |
| WO | WO2009/013397 | 1/2009 |
| WO | WO2009/144663 | 12/2009 |

*Primary Examiner* — Jerry Cumberledge  
*Assistant Examiner* — Tessa Matthews  
(74) *Attorney, Agent, or Firm* — Defillo & Associates, Inc; Evelyn A Defillo (57) ABSTRACT

The equipment includes at least one connecting bar, at least one flexible ligament, and at least one connector making it possible to connect the ligament to the connecting bar. The connector having a first conduit for engaging the connecting bar, equipped with a device for immobilizing the connector relative to the connecting bar, and a second conduit for receiving at least one strand of the ligament, having an insertion opening for this or these strands and an outlet opening for this or these strands, and equipped with devices for mobilizing the ligament relative to the connector. The second conduit is rectilinear between the insertion opening of the strand(s) of the ligament and the outlet opening. The second conduit has a transverse section adjusted to the transverse section of the strand(s) of the ligament that it is intended to receive, i.e. a transverse section just sufficient to allow sliding of the strand (s) of the ligament in the second conduit, but such that the strand(s) are in close contact with the walls delimiting the second conduit.

13 Claims, 4 Drawing Sheets

(56) References Cited

U.S. PATENT DOCUMENTS

| | | | |
|---|---|---|---|
| 8,110,946 B2* | 2/2012 | Morishima | 307/64 |
| 2002/0019633 A1* | 2/2002 | Ray | 606/53 |
| 2005/0129459 A1* | 6/2005 | Doubler et al. | 403/315 |
| 2008/0262553 A1* | 10/2008 | Hawkins et al. | 606/278 |
| 2009/0182379 A1* | 7/2009 | Baccelli et al. | 606/263 |
| 2009/0248077 A1* | 10/2009 | Johns | 606/246 |
| 2010/0121386 A1* | 5/2010 | Peultier et al. | 606/86 A |
| 2012/0059377 A1* | 3/2012 | Belliard | 606/74 |

* cited by examiner

VERTEBRAL OSTEOSYNTHESIS EQUIPMENT

CROSS REFERENCE TO RELATED APPLICATION

This application is a national stage entry of PCT/IB2012/052985 filed Jun. 13, 2012, under the International Convention claiming priority over French Application No. 1155504 filed Jun. 22, 2011.

FIELD OF THE INVENTION

The present invention relates to vertebral osteosynthesis equipment.

BACKGROUND OF THE INVENTION

To straighten a distracted spine, in particular in the case of scoliosis, it is well known to use vertebral osteosynthesis equipment including anchoring members for anchoring to the vertebrate (pedicle screws and/or lamina hooks), connecting bars, and connectors for connecting said bars to said anchoring members.

This type of equipment assumes that pedicles that are slightly or not at all deteriorated exist for anchoring screws, or that there are sufficient spaces at the laminas to engage the hooks behind said laminas. This type of equipment is therefore not suitable when the pedicles of the vertebrae are deteriorated or the spaces are insufficient at the vertebral laminas, as is the case when the spine is greatly distracted and/or when the vertebrae are significantly pivoted and/or deformed.

This type of equipment is also not suitable when it is necessary to perform a fairly significant "derotation" of one or more vertebrae, i.e. to pivot said vertebra(e) around themselves on the cervico-caudal axis so as to resituate them in normal anatomical positions.

For such indications of significantly distracted spines, significantly pivoted and/or deformed vertebrae, or significant "derotations," it is known from document EP 2 279 707 A1 to use equipment including, aside from connecting bars and connectors, flexible ligaments that can be engaged around the laminas of the vertebrae to be treated. These ligaments are connected, by the connectors, to a connecting bar which itself is connected to the healthy vertebrae situated at the ends of the vertebral segment be treated, and are used to perform traction on the series of vertebrae to be straightened. The straightening of this series of vertebrae is done progressively, by performing successive straightening operations on the vertebrae in intermediate straightening positions and by going from one vertebra to the next successively.

Such ligaments are in particular made up of plaits of polyester fibers, with a circular or flat section.

The existing equipment including these ligaments appears not to be fully satisfactory. In fact, the strength of the connection of the ligaments to the connectors appears uncertain over time. Furthermore, the force that must be exerted on a ligament to perform a derotation of a vertebra is significant, which makes that derotation operation relatively complex, difficult and long. Furthermore, the instruments used to act on the connectors when traction is exerted are not optimal.

OBJECTS OF THE INVENTION

The present invention therefore aims primarily to provide vertebral osteosynthesis equipment in which the strength of the connection of the ligaments to the connectors is durable.

Another aim of the invention is to provide equipment in which the force that must be exerted on a ligament to perform a derotation of a vertebra is more reduced than with the existing equipment.

One additional aim of the invention is to provide an instrument making the action exerted on the connectors easier to exert traction on a ligament.

SUMMARY OF THE INVENTION

The concerned equipment includes
at least one connecting bar,
at least one flexible ligament, and at least one connector making it possible to connect said ligament to said connecting bar, the connector including a first conduit for engaging the connecting bar, equipped with means for immobilizing the connector relative to said connecting bar, and a second conduit for receiving at least one strand of the ligament, having an insertion opening for this or these strands and an outlet opening for this or these strands;
the connector includes a first portion in which said first conduit is formed and a second portion in which the second conduit is formed, said second conduit being separate from the first conduit and not in communication therewith;
said second conduit is equipped with means for immobilizing the ligament relative to the connector, including a tightening member exerting, when it is tightened, a gripping of the ligament in said second conduit along an axis perpendicular to said second conduit.
According to the invention,
said second conduit is rectilinear between said insertion opening and said outlet opening, and
said second conduit has a transverse section adjusted to the transverse section of the strand(s) of the ligament that it is intended to receive, i.e. a transverse section just sufficient to allow sliding of the strand(s) of the ligament in said second conduit, but such that the strand(s) are in close contact with the walls delimiting said second conduit.

Thus, according to the invention, said second conduit is completely separate from said first conduit and is rectilinear, such that it does not have any sharp edges capable of making localized contact of the connector with the ligament, risking creating wear of the material of the ligament under the combined effect of the tension undergone by the ligament and the repeated forces exerted on that ligament by the movements of the patient; the tightening member may perform tightening of the ligament perpendicular to said second conduit, and the adjusted section of said second conduit makes it possible to ensure positioning of the ligament that is perfectly perpendicular to the tightening member, and to perform lateral setting of the ligament, therefore to oppose excessive crushing of the ligament by said member.

It emerges from all of these features that the equipment according to the invention eliminates any localized wear of the ligament and that it thereby makes it possible to obtain lasting strength of the connection of the ligament with the connector.

It will be understood that, according to a first possibility, the ligament is a single strand, having one end fastened to the vertebra, or has two strands, but with a single strand engaged in the connector, the other strand for example being fastened to the connector; in that case, the connector is of a first type, in which said second conduit has a transverse section adjusted to the transverse section of the single strand that passes through said second conduit. According to another possibility, the ligament has two strands and said two strands are engaged in the connector; the connector is then of a second type, in which said second conduit has a transverse section adjusted to the transverse section of the two strands that pass through said second conduit.

It will also be understood that the expression "adjusted transverse section" designates the fact that, when a single strand of the ligament is engaged in said second conduit, that strand is in close contact, by its four longitudinal sides, with the walls of the connector delimiting said second conduit, and that, when the two strands of the ligament are engaged in said second conduit, those strands are in close contact with one another by one of their longitudinal sides and are in close contact, by their other three longitudinal sides, with the walls of the connector delimiting said second conduit.

Preferably, the connector forms a planar surface delimiting said second conduit, situated opposite said tightening member.

The strand(s) of the ligaments are thus tightened in perfect conditions, between the tightening member and said planar surface delimiting said second conduit.

Preferably, the insertion opening of said strand(s) of the ligament into said second conduit, i.e. the opening situated closest to a vertebra during use of the equipment, is delimited by a rounded edge.

This edge also makes it possible to reduce the risk of localized wear of the material of the ligament.

Preferably, said tightening member has a diameter larger than the width of the strand of the ligament engaged in said second conduit, or, when the two strands of the ligament are engaged in said conduit side-by-side, has a diameter larger than the cumulative width of said two strands.

In this way, there is no risk of the member sectioning said strand(s).

Preferably,
said means for immobilizing the ligament include a tapped bore formed in said second portion, with an axis perpendicular to said second conduit and communicating with that conduit, and
said tightening member is a screw capable of being received in said bore, having a planar and smooth inner end surface.

The tightening screw can have a rounded edge between its smooth inner planar end surface and its adjacent peripheral surface.

This tightening screw can also have a thread extending only over a proximal portion of its length, the peripheral surface of the distal portion of the screw, adjacent to said smooth planar inner end surface, being smooth.

In this way, there is no risk of the fibers of the ligament being deteriorated or sectioned by the end of the thread of the screw.

Advantageously, in that case, said tapped bore includes, at the bottom thereof, a smooth portion with a diameter adjusted to that of the smooth distal portion of the tightening screw.

This smooth portion makes it possible to avoid any risk of the fibers of the ligament rising up between the threads of the screw and the tapped portion of the bore during tightening of the screw.

Said second conduit could be formed in a direction substantially perpendicular to a length of the connector defined jointly by said first portion and second portion; preferably, however, this second conduit is arranged obliquely relative to said length, such that the insertion opening of the strand(s) of the ligament in said second conduit, i.e. the opening located closest to a vertebra during the use of the equipment, emerges on one side of said second portion substantially opposite said first portion, or distant from said first portion.

Said opening is less distant from the conduit formed by said first portion, which makes it possible to generate a significant lever arm when a pivot force is exerted on the connector in order to exert traction on the ligament. This lever arm consequently makes it possible to reduce the force that must be exerted on a connector to perform a derotation operation of a vertebra, and therefore to facilitate that operation.

The angle of said second conduit with the direction of said length can in particular be between 30° and 60°. Preferably, this angle is 45°.

Preferably, the equipment according to the invention includes:
  a lever whereof one end is configured to engage with the connector so as to connect that connector with that lever pivotably along the axis of said first conduit, while leaving free access to said means for immobilization of the connector relative to said connecting bar and said tightening member, such that maneuvering these immobilization means and this tightening member in order to perform this immobilization and tightening is possible when the lever is engaged with the connector, while leaving free access to the ligament, such that the latter can be stressed; and
  instruments for maneuvering said immobilization means and said tightening screw when said lever is engaged with the connector.

The equipment according to the invention thus makes it possible to perform a rotation of a vertebra using the following sequence of operations:
  engaging the connector on a connecting bar, then connecting said bar to help the vertebrae situated on either side of the vertebra to be straightened, and engaging the ligament connected to that vertebra in said second conduit of the connector;
  engaging the lever on the connector then, said immobilization means being released such that pivoting of the connector relative to the connecting bar is possible, performing pivoting of the connector toward the vertebra in the direction shortening the portion of the ligament extending between the vertebrae in the connector;
  in that position of the connector, stressing the ligament and tightening said tightening member;
  pivoting the connector using the lever in the opposite direction, performing pivoting of the vertebra with the connector toward a straightened position of the vertebra;
  in this straightening position thus achieved by the connector and the vertebra, maneuvering said immobilization means so as to immobilize the connector, and therefore the vertebra, in this straightening position.

Said end of the lever is preferably in the form of an open cage delimited by two parallel walls capable of closely hugging the shape of the side surfaces of the connector, and by a bearing wall capable of bearing on said second portion of the connector, said bearing wall including a notch allowing access to said tightening screw.

The two parallel walls advantageously include notches allowing their adjusted engagement on the connecting bar, said notches ensuring pivoting guiding of the lever relative to the axis of said bar.

The invention will be well understood, and other features and advantages thereof will appear, in reference to the appended diagrammatic drawing, showing, as a non-limiting example, one preferred embodiment of the equipment it concerns.

DESCRIPTION OF THE PREFERRED EMBODIMENTS

Figure 1:
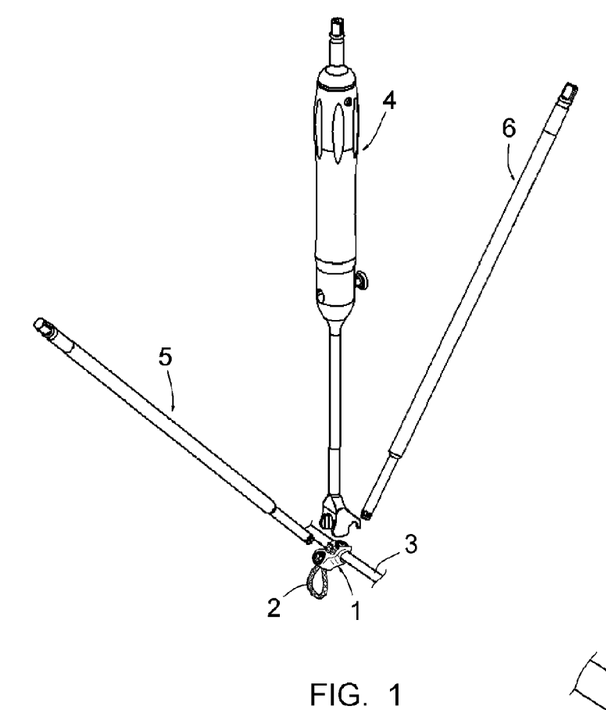
FIG. 1 is a perspective view of a connector, a ligament, a portion of a connecting bar, a lever and two maneuvering instruments comprised by said equipment.
Figure 2:
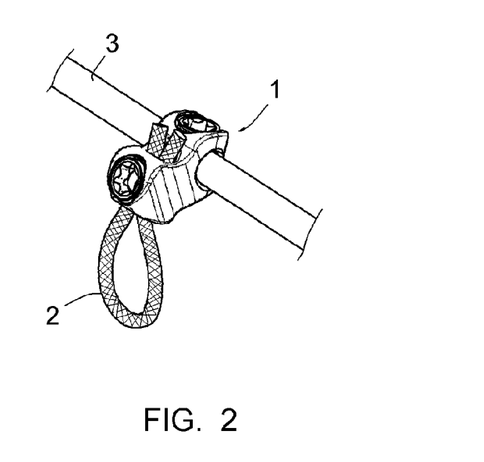
FIG. 2 is a view of the connector, the ligament, and the portion of the connecting bar on a larger scale.

FIG. 1 shows a connector 1, a ligament 2, a portion of a connecting bar 3, a lever 4 and two maneuvering instruments 5, 6 of a piece of vertebral osteosynthesis equipment. This equipment also includes anchor members for anchoring the bar 3 to the vertebrae, in particular pedicle screws and/or lamina hooks (not shown). It includes a plurality of connectors 1, ligaments 2, and levers 4, making it possible to treat a plurality of vertebrate simultaneously, as well as a second connecting bar and other anchor members for anchoring said second part of the vertebrae, making it possible to anchor said second bar on the sides of the vertebrae opposite that on which the bar 3 is installed.

Figure 4:
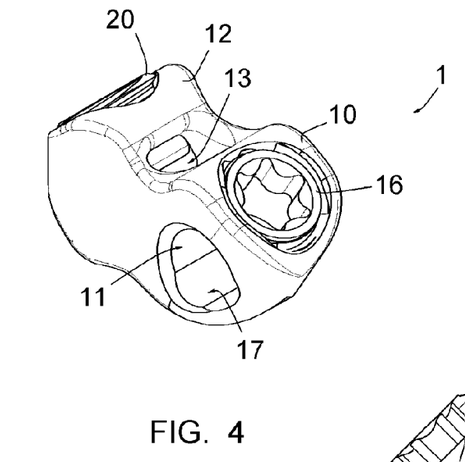
FIG. 4 is a perspective view of the connector, on an even larger scale.
Figure 5:
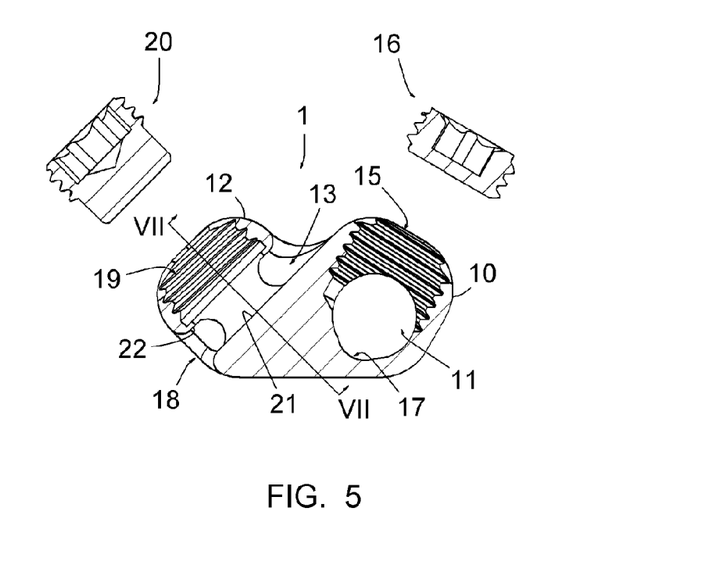
FIG. 5 is a view of the connector in longitudinal cross-section, two tightening screws of that connector being out of their tapped receiving bores.
Figure 6:
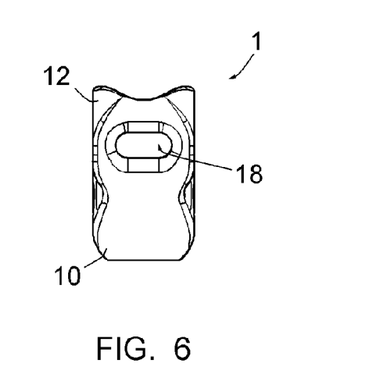
FIG. 6 is a side view, along the axis of the conduit of said connector.

FIGS. 4 to 6 show that the connector 1 includes a first portion 10, in which a first conduit 11 is formed for engaging on the bar 3, and a second portion 12 in which a second conduit 13, for receiving the two strands of the ligament 2, is formed, side-by-side.

The first conduit 11 communicates with a tapped bore 15 for receiving a screw 16 for tightening the bar 3 in said conduit 11. This conduit 11 includes, on the side diametrically opposite the bore 15, a rounded longitudinal recess 17 whereof the connection to the rest of the conduit 11 forms two longitudinal edges. The presence of these edges is favorable to complete immobilization of the connector 1 in rotation relative to the bar 3 when the screw 16 is tightened.

The second conduit 13 is separate from the first conduit 11 and is not in communication therewith. It is rectilinear between the opening 18 for insertion therein of the strands of the ligament 2 and the opening opposite that conduit 13. The latter is also formed at 45° relative to a length of the connector 1 defined jointly by said first portion 10 and second portion 12, such that the opening 18 emerges on a side of the second portion 12 substantially opposite the first portion 10, or remote from said first portion 10.

The opening 18 is delimited by a rounded edge over the entire periphery thereof, as visible in FIG. 6.

Figure 7:
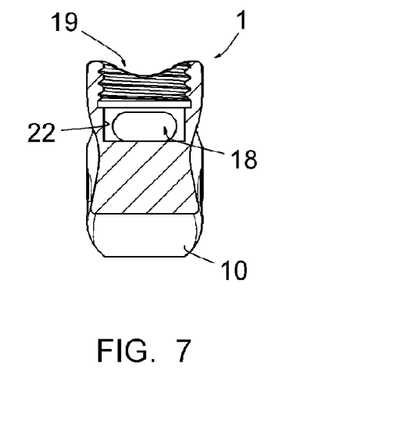
FIG. 7 is a cross-sectional view along line VII-VII of FIG. 5.
Figure 8:
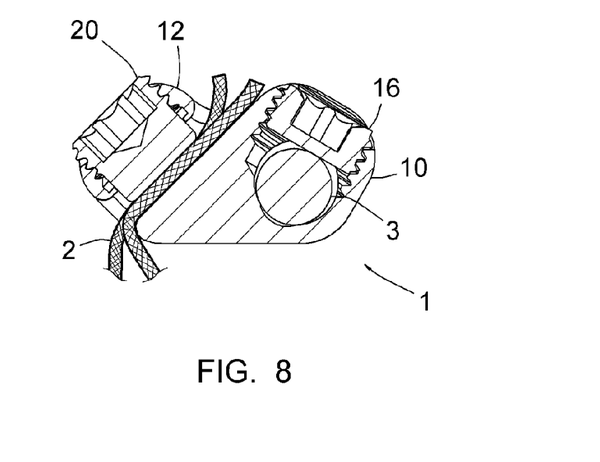
FIG. 8 is a view similar to FIG. 5 when the connector is engaged on the connecting bar, the ligament is engaged thereon, and the tightening screws are placed in said bores.
Figure 9:
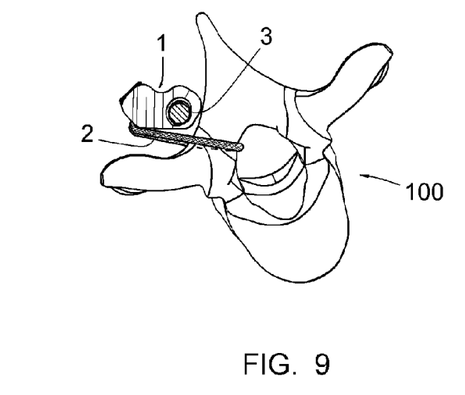
FIGS. 9 to 12 are views of a vertebra and the aforementioned elements of the equipment during four successive steps of the derotation of the vertebra, with a sub-lamina ligament passage.
Figure 10:
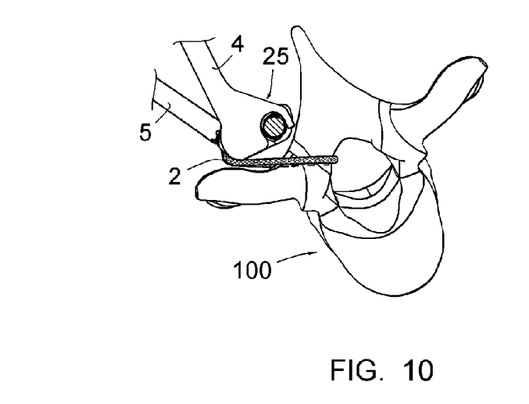
Figure 11:
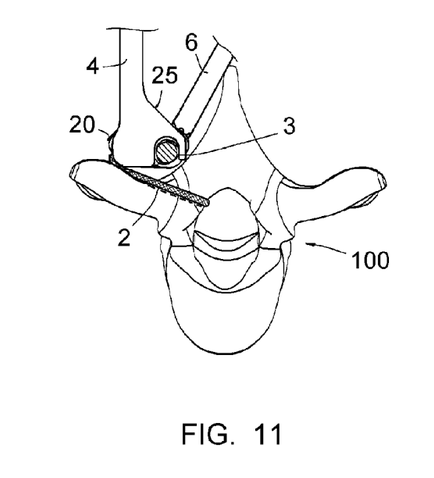

The conduit 13 communicates with a tapped bore 19 with an axis perpendicular thereto, intended to receive a screw 20 for tightening the ligament 2 therein. On the side of the first portion 10, this conduit 13 is delimited by a planar surface 21 extending in the continuation of the lower edge of the opening 18 (cf. FIG. 7). The conduit 13 also has a section adjusted to the section of the two strands of the ligament 2 it is intended to receive side-by-side.

The screw 20 has a diameter larger than the cumulative width of the two strands of the ligament, and has a thread extending only over a proximal portion of its length, the distal portion of said screw having a smooth peripheral surface. The screw 20 ends with a smooth planar end surface, perpendicular to the axis of the screw, connected to the smooth peripheral surface by a rounded edge.

The second portion 12 of the connector 1 also has, at the bottom of the bore 19, a smooth portion 22 defining an opening with a diameter adjusted to that of the smooth distal portion of the screw 20.

As understood in reference to FIG. 6, all of these arrangements (with the exception of the incline of the conduit 13) make it possible to eliminate any localized contact of the ligament 2 with the connector, and therefore any risk of localized wear of the material of the ligament 2, and makes it possible to thereby obtain a durable strength of the connection of said ligament with the connector 1. In fact:

the strands of the ligament 2 are tightened between extended tightening surfaces, formed by the smooth planar end surface of the screw 20 and by the planar surface 21 situated opposite it;

positioning of the ligament 2 completely perpendicularly to the screw 20 is ensured;

no sharp edges are likely to make localized contact of the connector 1 with the ligament 2;

the section of the conduit 13 adjusted to the section of the strands of the ligament 2 makes it possible to oppose excessive crushing of the ligament 2 by the screw 20, thereby performing lateral setting of the ligament 2; and any risk of deterioration or sectioning of the fibers of the ligament 2 by the end of the thread of the screw 20 is eliminated, owing to the absence of thread on the distal portion of the screw 20 and the barrier formed by the smooth portion 22.

The incline of the conduit 13 makes it possible to create a significant lever arm when a pivot force is exerted on the connector 1 in order to exert traction on a vertebra to be straightened, as will be described later in reference to FIGS. 9 to 12 or 13 to 16.

The ligament 2 is, in a known manner, made up of a plait of polyester fibers, with a circular section in the illustrated example.

The bar 3 is, in a manner also well known, formed by a metal cylinder.

Figure 3:
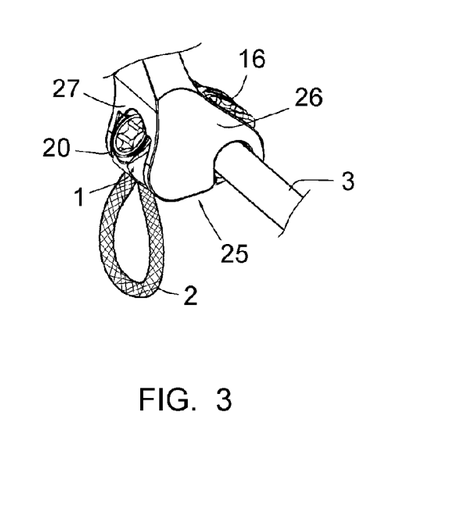
FIG. 3 is a view of the connector, the ligament, and the portion of the connecting bar similar to FIG. 2, after the lever engages with the connector.

The lever 4 has a distal end 25 configured in an open cage capable of being closely engaged on the connector 1, as shown in FIG. 3, and engaging therewith so as to pivotably connect the connector 1 and the lever 4 along the axis of the conduit 11. The open cage is delimited by two parallel walls 26 capable of closely hugging the side surfaces of the connector 1 and a bearing wall 27 capable of bearing on said second portion 12 of the connector. The two parallel walls 26 include notches allowing them to be engaged in an adjusted manner on the bar 3, these notches thereby ensuring pivoting guiding of the lever 4 relative to the axis of said bar 3.

The bearing wall 27 includes a notch allowing access to the screw 20, and, on the side opposite the wall 27, said open cage forms a wide access opening for accessing the screw 16.

The maneuvering instruments 5, 6 assume the form of rods including, at their distal ends, portions engaged with the maneuvering cavities comprised by the screws 16 and 20, and at their proximal ends, square-shaped actuating portions. Said engaging portions and said maneuvering cavities are star-shaped profiles called "torks" in the illustrated example.

FIGS. 9 to 12, or 13 to 16, respectively illustrate four steps of a procedure for derotation of one or more vertebrate 100 that the equipment according to the invention makes it possible to perform, i.e. pivoting of said vertebra(e) 100 around themselves substantially along their cervico-caudal axis in order to resituate said vertebrate in anatomically normal positions.

Figure 12:
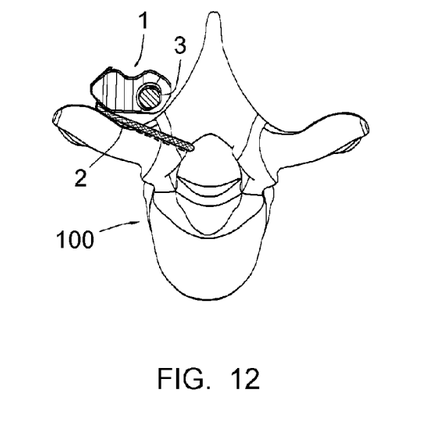
Figure 13:
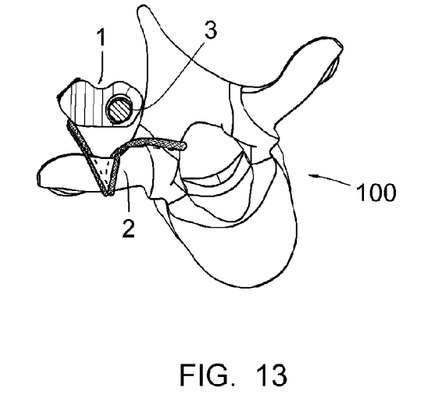
FIGS. 13 to 16 are views similar to FIGS. 9 to 12 respectively, of a sub-lamina ligament passage and are transverse views.
Figure 14:
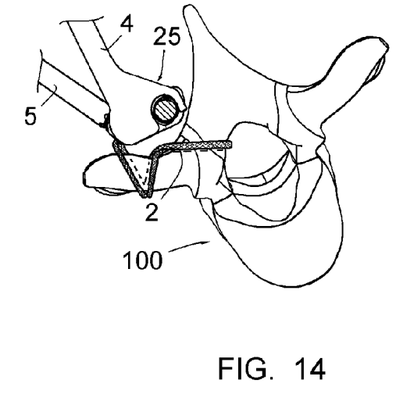
Figure 15:
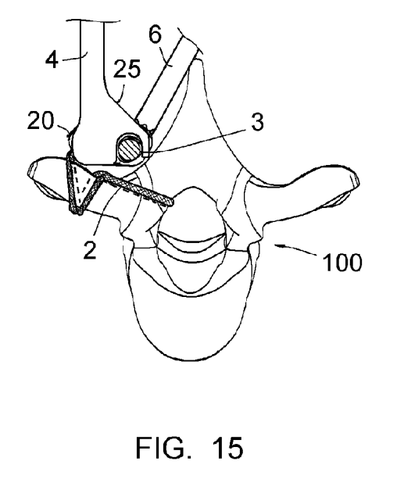
Figure 16:
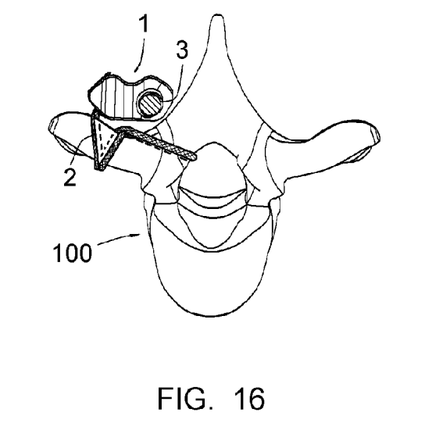

This procedure is done the using the following sequence of operations:
- placing bone anchoring members (not shown) in healthy vertebrae situated on either side of the vertebra(e) 100 to be straightened and mounting the bar 3 on said anchoring members, with, mounted on said bar 3, the number of connectors 1 corresponding to the number of vertebrae 100 to be straightened;
- placing a second connecting bar and other anchoring members of said second bar at said healthy vertebrae, on the side of the vertebrae opposite that on which the bar 3 is installed (this second connecting bar and these other anchor members are not shown in the figures);
- engaging each ligament 2 around the lamina of the corresponding vertebra and engaging, in the conduit 13, the connector 1 through the opening 18 (cf. FIG. 9);
- engaging each lever 4 on the corresponding connector 1, then, the screw 16 being unscrewed such that it is possible to pivot the connector 1 relative to the bar 3, pivoting the connector 1 toward the vertebra 100 in the direction shortening the portion of the ligament 2 extending between the vertebrate 100 and the connector 1;
- in this position of the connector 1, stressing the ligament 2 and tightening the screw 20 using the instrument 5 (cf. FIG. 10);
- pivoting the connector 1 using the lever 4 in the opposite direction, causing the vertebra 100 to pivot with the connector 1 toward a straightening position of the vertebra 100;
- in this straightening position thus achieved by the connector 1 and the vertebra 100, tightening the screws 16 so as to immobilize the connector 1, and therefore the vertebra 100, in this straightening position (cf. FIG. 11);
- removing the lever 4 (cf. FIG. 12).

To simplify the description of this derotation procedure, pivoting of the vertebra 100 has been shown directly into a final straightening position; in practice, this straightening is generally done over several vertebrae, and is done gradually, by successive straightening operations of the vertebrae in intermediate straightening positions and progressing from one vertebra to the next, successively.

As previously indicated, the opening 18 of the conduit 13 is distant from the conduit 11, which makes it possible, as shown in FIGS. 7 to 10, to generate a significant lever arm when the pivot force is exerted on the connector 1 using the lever 4. This lever arm consequently makes it possible to reduce the force that must be exerted on the connector 1 to perform the derotation operation, and therefore greatly facilitate the operation.

FIGS. 13 to 16 are views similar to FIGS. 9 to 12, respectively, except that the ligament 2 is engaged around the lamina of the corresponding vertebra and around the transverse apophysis, with crossing of the strands between the lamina and the transverse apophysis and passage of the strands on each side of said transverse apophysis.

The invention consequently provides vertebral osteosynthesis equipment having the decisive advantages of allowing a durable connection of the ligament 2 to a connector 1, making it possible to exert a more reduced force on said ligament during a derotation operation of a vertebra, and making the action exerted on a connector 1 to perform traction on the ligament 2 easier.

The invention has been described above in reference to one embodiment provided as an example. It is of course in no way limited to that embodiment, but on the contrary encompasses all other embodiments covered by the appended claims.

What is claimed is:

1. An equipment for a vertebral osteosynthesis comprising:
at least one connecting bar,
at least one flexible ligament,
at least one connector to connect said flexible ligament to said connecting bar, the connector including:
a first portion including a first conduit for engaging the connecting bar, a first tapped bore, and an immobilizing device connected to the first tapped bore to immobilize the connector relative to said connecting bar,
a second portion including a second conduit to receive at least one strand of the flexible ligament, the second conduit includes an insertion opening, an outlet opening, and a tapped bore, the tapped bore is perpendicular to the second conduit,
said second conduit being separate from the first conduit;
a tightening member to immobilize the ligament relative to the connector;
wherein:
said second conduit is separated from the first conduit by a planar surface which extends from a lower edge of the insertion opening to the outlet opening;
the tightening member is situated opposite to said planar surface;
said insertion opening is for inserting the at least one strand of the ligament to the connector and said outlet opening is for letting the at least one strand to extend outside the connector from said second conduit;
said second conduit is rectilinear between said insertion opening and said outlet opening,
said tightening member means, is connected to the tapped bore of said second portion;
said tightening member is a screw having a length with thread extending only over a proximal portion of the length;
said second conduit has a transverse section adjusted to a transverse section of the at least one strand of the ligament that it is intended to receive, the transverse section has just a sufficient width to allow sliding of the at least one strand of the ligament in said second conduit, the at least one strand is in close contact with walls delimiting said second conduit.

2. The equipment according to claim 1 wherein said insertion opening, which is situated closest to a vertebra during use of the equipment, is delimited by a rounded edge.

3. The equipment according to claim 1 wherein said tightening member has a diameter larger than a width of the strand of the ligament engaged in said second conduit, or, when a two strands of the ligaments are engaged in said second conduit side-by-side, has a diameter larger than a cumulative width of said two strands.

4. The equipment according to claim 1, wherein the tightening screw has a rounded edge between a smooth planar inner end surface and an adjacent peripheral surface.

5. The equipment according to claim 1, wherein the tightening screw has a thread extending only over a proximal portion of its length, a peripheral surface of a distal portion of the screw, adjacent to a smooth planar inner end surface, being smooth.

6. The equipment according to claim 5 wherein said tapped bore includes, at a bottom thereof, a smooth portion with a diameter adjusted to that of a smooth distal portion of the tightening screw.

7. The equipment according to claim 1 wherein the second conduit is arranged obliquely relative to said length, such that said insertion opening, which located closest to a vertebra during the use of the equipment, emerges on one side of said second portion substantially opposite said first portion, or distant from said first portion.

8. The equipment according to claim 7 wherein an angle of said second conduit with a direction of said length is between 30° and 60°.

9. The equipment according to claim 7, wherein an angle of said second conduit with the direction of said length is 45°.

10. An equipment for a vertebral osteosynthesis comprising:
at least one connecting bar,
at least one flexible ligament,
at least one connector to connect said flexible ligament to said connecting bar, the connector including:
a first portion including a first conduit for engaging the connecting bar, a first tapped bore, and an immobilizing device connected to the first tapped bore to immobilize the connector relative to said connecting bar,
a second portion including a second conduit to receive at least one strand of the flexible ligament, the second conduit includes an insertion opening, an outlet opening, and a tapped bore, the tapped bore is perpendicular to the second conduit,
said second conduit being separate from the first conduit;
a lever having an end configured to pivotably connect to the connector, the lever pivots along an axis of said first conduit, while leaving free access to the immobilizing device of the connector relative to said connecting bar and said tightening member, such that maneuvering the immobilization device means and the tightening member in order to perform this immobilization and tightening is possible when the lever is engaged with the connector, while leaving free access to the ligament, such that the latter can be stressed;
instruments for maneuvering said immobilization device and said tightening screw when said lever is engaged with the connectors;
a tightening member to immobilize the ligament relative to the connector;
wherein:
said second conduit is separated from the first conduit by a planar surface which extends from a lower edge of the insertion opening to the outlet opening;
the tightening member is situated opposite to said planar surface;
said insertion opening is for inserting the at least one strand of the ligament to the connector and said outlet opening is for letting the at least one strand to extend outside the connector from said second conduit;
said second conduit is rectilinear between said insertion opening and said outlet opening,
said tightening member is connected to the tapped bore of said second portion;
said tightening member is a screw having a length with thread extending only over a proximal portion of the length;
said second conduit has a transverse section adjusted to a transverse section of the at least one strand of the ligament that it is intended to receive, the transverse section has just a sufficient width to allow sliding of the at least one strand of the ligament in said second conduit, the at least one strand is in close contact with walls delimiting said second conduit.

11. The equipment according to claim 10, wherein said end of the lever is in the form of an open cage, delimited by two parallel walls, capable of closely hugging a shape of side surfaces of the connector, and by a bearing wall capable of bearing on said second portion of the connector, said bearing wall including a notch allowing access to said tightening screw.

12. The equipment according to claim 11 wherein the two parallel walls advantageously include notches allowing their adjusted engagement on the connecting bar, said notches ensuring pivoting guiding of the lever relative to an axis of said bar.

13. A method for derotation of a vertebrate, i.e. pivoting of said vertebra(e) around themselves substantially along their cervico-caudal axis in order to resituate said vertebrate in anatomically normal positions, wherein the method includes the following steps:
using an equipment for a vertebral osteosynthesis comprising: at least one connecting bar; at least one flexible ligament, at least one connector to connect said flexible ligament to said connecting bar, the connector including: a first portion including a first conduit for engaging the connecting bar and an immobilizing device to immobilize the connector relative to said connecting bar, and a second portion including a second conduit to receive at least one strand of the flexible ligament, the second conduit includes an insertion opening and an outlet opening; said second conduit being separate from the first conduit and not in communication therewith; said second conduit includes a tightening member to immobilize the ligament relative to the connector; wherein: said insertion opening is for inserting the at least one strand in the connector and opens on an outside of the connector, and said outlet opening is for letting the at least one strand to extend outside the connector from said second conduit and opens on the outside of the connector;
said second conduit is rectilinear between said insertion opening and said outlet opening; said tightening member for immobilizing the ligament is connected to a tapped bore formed in said second portion, with an axis perpendicular to said second conduit and having an inner portion communicating with the second conduit; said tightening member is a screw capable of being received in said bore, having a planar and smooth inner end surface, and said second conduit has a transverse section adjusted to a transverse section of the at least one strand of the ligament that it is intended to receive, the transverse section has just a sufficient width to allow sliding of the at least one strand of the ligament in said second conduit, the at least one strand is in close contact with walls delimiting said second conduit;

engaging the connector on a connecting bar, then connecting said bar to help the vertebrae situated on either side of the vertebra to be straightened, and engaging the ligament connected to that vertebra in said second conduit of the connector;

engaging a lever on the connector then, releasing said tightening member such that pivoting of the connector relative to the connecting bar is possible, pivoting the connector toward the vertebra in the direction shortening the portion of the ligament extending between the vertebrae in the connector;

in that position of the connector, stressing the ligament and tightening said tightening member;

pivoting the connector using the lever in the opposite direction, performing pivoting of the vertebra with the connector toward a straightened position of the vertebra;

in this straightening position thus achieved by the connector and the vertebra, maneuvering said immobilization device so as to immobilize the connector, and therefore the vertebra, in this straightening position.

\* \* \* \* \*